United States Patent
Huang et al.

(10) Patent No.: US 11,110,047 B2
(45) Date of Patent: Sep. 7, 2021

(54) ORAL CARE COMPOSITIONS INCLUDING CYCLIC ANHYDRIDES

(71) Applicant: Colgate-Palmolive Company, New York, NY (US)

(72) Inventors: Chun Huang, Somerset, NJ (US); Guofeng Xu, Plainsboro, NJ (US); Cajetan Dogo-Isonagie, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/670,009

(22) Filed: Aug. 7, 2017

(65) Prior Publication Data

US 2019/0038535 A1 Feb. 7, 2019

(51) Int. Cl.
- *A61K 8/49* (2006.01)
- *A61K 8/21* (2006.01)
- *A61K 8/22* (2006.01)
- *A61Q 11/00* (2006.01)

(52) U.S. Cl.
CPC .............. *A61K 8/4973* (2013.01); *A61K 8/21* (2013.01); *A61K 8/22* (2013.01); *A61Q 11/00* (2013.01)

(58) Field of Classification Search
CPC ................................. A61K 8/22; A81Q 11/00
USPC ........................................................ 424/53
See application file for complete search history.

(56) References Cited

U.S. PATENT DOCUMENTS

| | | | | |
|---|---|---|---|---|
| 3,513,136 A | * | 5/1970 | Blumbergs | C08F 22/04 250/396 R |
| 4,218,434 A | * | 8/1980 | Rolla | A61Q 11/00 424/49 |
| 5,302,375 A | | 4/1994 | Viscio | |
| 5,736,158 A | * | 4/1998 | Quast | A61K 8/21 424/464 |
| 5,827,505 A | * | 10/1998 | Hughes | A61K 8/22 424/49 |
| 6,221,341 B1 | | 4/2001 | Montgomery | |
| 6,475,472 B2 | | 11/2002 | Joiner et al. | |
| 9,161,892 B2 | * | 10/2015 | Simon | A61K 8/24 |
| 2002/0187108 A1 | * | 12/2002 | Rajaiah | A23G 4/02 424/49 |
| 2010/0092407 A1 | * | 4/2010 | Kurata | A61K 8/362 424/53 |
| 2014/0314829 A1 | | 10/2014 | Boyd et al. | |
| 2016/0324740 A1 | | 11/2016 | Ontumi et al. | |

FOREIGN PATENT DOCUMENTS

| EP | 1738802 | 1/2007 |
|---|---|---|
| EP | 2130528 | 12/2009 |
| JP | S52-102439 | 8/1977 |

OTHER PUBLICATIONS

International Search Report and Written Opinion of the International Searching Authority in International Application No. PCT/US2017/045661, dated Jan. 15, 2018.

* cited by examiner

*Primary Examiner* — Walter E Webb

(57) ABSTRACT

A whitening composition and methods for whitening teeth and generating a whitening agent with the same are provided. The whitening composition may include an orally acceptable vehicle, a source of hydrogen peroxide that provides hydrogen peroxide, and a cyclic anhydride that generates a whitening agent with the hydrogen peroxided provided by the source of hydrogen peroxide. The whitening agent may be a peracid, such as a succinic peracid.

14 Claims, No Drawings

ORAL CARE COMPOSITIONS INCLUDING CYCLIC ANHYDRIDES

BACKGROUND

Conventional oral care products (e.g., toothpastes, whitening gels, whitening trays, etc.) and whitening agents thereof are often utilized to whiten teeth. For example, conventional mouthwashes including hydrogen peroxide are often utilized to oxidize chromophores bound to surfaces of teeth to thereby whiten the teeth. While mouthwashes including hydrogen peroxide have proven to be effective for whitening teeth, different chromophores on the surfaces are often oxidized at varying rates and/or via varying mechanisms. Accordingly, mouthwashes including a single whitening agent (e.g., hydrogen peroxide) may require relatively longer periods of treatment to appreciably whiten the teeth.

In view of the foregoing, oral care products incorporating hydrogen peroxide often include an additional whitening agent to facilitate the oxidation of the different chromophores to thereby shorten the periods of treatment. While the oral care products incorporating a variety of whitening agents have demonstrated increased efficacy in whitening teeth, there is a desire to utilize whitening agents having relatively increased reactivity to thereby further reduce the periods of treatment. The whitening agents having relatively increased reactivity, however, are often unstable and subject to degradation. For example, the whitening agents having relatively increased reactivity often react with other components of the oral care products and/or degrade, thereby reducing the effectiveness thereof.

What is needed, then, are improved oral care products and whitening compositions thereof, and methods for generating whitening agents from the whitening compositions.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a whitening composition including an orally acceptable vehicle, a source of hydrogen peroxide that provides, is capable of providing, or configured to provide hydrogen peroxide, and a cyclic anhydride that generates a peracid with the hydrogen peroxide provided by the source of hydrogen peroxide.

In at least one implementation, the source of hydrogen peroxide includes at least one of hydrogen peroxide, urea peroxide, calcium peroxide, sodium perborate, a polyvinylpyrrolidone (PVP) hydrogen peroxide complex, and sodium percarbonate.

In at least one implementation, the source of hydrogen peroxide is present in the whitening composition in an amount effective to provide less than or equal to 2.0 weight % of the hydrogen peroxide, based on a total weight of the whitening composition.

In at least one implementation, the cyclic anhydride is at least one of maleic anhydride, succinic anhydride, naphthalenetetracarboxylic dianhydride, phthalic anhydride, chloromaleic anhydride, dichloromaleic anhydride, and a polymer-based cyclic anhydride.

In at least one implementation, the cyclic anhydride is maleic anhydride.

In at least one implementation, the peracid is maleic peracid.

In at least one implementation, the cyclic anhydride is succinic anhydride.

In at least one implementation, the peracid is succinic peracid.

In at least one implementation, a molar ratio of the cyclic anhydride to the hydrogen peroxide provided by the source of hydrogen peroxide is from about 0.1:1 to about 2:1, about 0.8:1 to about 1.3:1, or about 1:1.

In at least one implementation, the whitening composition is a mouthwash.

In at least one implementation, the peracid is generated in less than or equal to three minutes after contacting the hydrogen peroxide and the cyclic anhydride with one another.

In at least one implementation, the whitening composition further includes a fluoride ion source.

In at least one implementation, the whitening composition further includes a surfactant.

The foregoing and/or other aspects and utilities embodied in the present disclosure may also be achieved by providing a method for whitening teeth of a subject, including contacting any of the whitening compositions disclosed herein with surfaces of the teeth of the subject in need thereof.

The foregoing and/or other aspects and utilities embodied in the present disclosure may also be achieved by providing a method for generating a whitening agent in a whitening composition. The method may include contacting a cyclic anhydride and hydrogen peroxide with one another to generate the whitening agent. The whitening agent generated by contacting the cyclic anhydride and the hydrogen peroxide may be a peracid.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout, ranges are used as shorthand for describing each and every value that is within the range. Any value within the range may be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that whitening composition including a source of hydrogen peroxide and a cyclic anhydride provides a significant and unexpected increase or enhancement in whitening efficacy of teeth as compared to whitening compositions including the source of hydrogen peroxide alone.

Compositions

Compositions disclosed herein may be or include an oral care product or a whitening composition thereof. For example, the composition may be an oral care product (e.g., a dentifrice, a prophylactic paste, a mouthwash, etc.) including the whitening composition, or the whitening composition thereof. The whitening composition may include one or more sources of hydrogen peroxide and one or more cyclic anhydrides. As further described herein, hydrogen peroxide from the one or more sources of hydrogen peroxide and the one or more cyclic anhydrides may react with one another to generate a whitening agent (e.g., peracid).

In at least one implementation, the source of hydrogen peroxide and the cyclic anhydride may be maintained separate from one another until the point of use, and at the point of use, the source of hydrogen peroxide and the cyclic anhydride may be contacted, mixed, or otherwise combined with one another. The source of hydrogen peroxide and the cyclic anhydride may be maintained in separate phases or components of the whitening composition until the point of use. For example, the source of hydrogen peroxide and the cyclic anhydride may be maintained in separation phases, such as a hydrophobic phase and a hydrophilic phase, until the point of use. In another example, the source of hydrogen peroxide and the cyclic anhydride may be maintained and stored in separate vessels or containers until the point of use. Prior to or at the point of use, the respective contents of the separate vessels or containers may be combined or otherwise contacted with one another to generate the whitening agent.

In at least one implementation, the oral care product, the whitening composition thereof, or a component thereof, prior to use, may be anhydrous. For example, the oral care product may be a dentifrice that is free or substantially free of water. In another example, a hydrophobic phase of the oral care product or the whitening composition thereof may be free or substantially free of water. As used herein, "free" or "substantially free" may refer to a composition, component, or phase that contains less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the whitening composition, component, or phase.

In one implementation, contacting at least a portion or component of the whitening composition with water may initiate the release of hydrogen peroxide. For example, contacting the one or more sources of hydrogen peroxide with water may initiate the release of hydrogen peroxide. In another example, contacting at least a portion of the whitening composition with water initiates the generation of the whitening agent (e.g., peracid). In yet another example, the sources of hydrogen peroxide and the cyclic anhydride be maintained in separate phases, such as hydrophobic and hydrophilic phases, and combining, mixing, or otherwise contacting the hydrophobic phase and hydrophilic phase with one another may initiate the release of hydrogen peroxide.

Sources of Hydrogen Peroxide

The one or more sources of hydrogen peroxide may be any compound or material capable of or configured to generate hydrogen peroxide to react with the cyclic anhydride to generate the whitening agent. For example, the source of hydrogen peroxide may be or include any compound capable of or configured to provide or release hydrogen peroxide to react with the cyclic anhydride. Illustrative sources of hydrogen peroxide may be or include, but are not limited to, hydrogen peroxide, urea peroxide, calcium peroxide, sodium perborate, a cross-linked polyvinylpyrrolidone (PVP) hydrogen peroxide complex, a polyvinylpyrrolidone (PVP) hydrogen peroxide complex, sodium percarbonate, and the like, and combinations thereof. The sources of hydrogen peroxide may also be or include, but are not limited to, PEROXYDONE™ XL 10F complex, which is commercially available from Ashland Inc. of Covington, Ky. In a typical implementation, the source of hydrogen peroxide includes hydrogen peroxide.

The amount or concentration of the source of hydrogen peroxide may vary widely, and may depend upon the amount of hydrogen peroxide provided or otherwise delivered by the source of hydrogen peroxide. In at least one implementation, the source of hydrogen peroxide may be present in an amount that provides from greater than 0.0 weight % to less than or equal to 10.0 weight free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from greater than 0.0 weight %, about 0.5 weight %, about 1.0 weight %, about 1.5 weight %, about 2.0 weight %, about 2.5 weight %, about 3.0 weight %, about 3.5 weight %, about 4.0 weight %, or about 4.5 weight % to about 5.5 weight %, about 6.0 weight %, about 6.5 weight %, about 7.0 weight %, about 7.5 weight %, about 8.0 weight %, about 85 weight %, about 9.0 weight %, about 9.5 weight %, or about 10.0 weight %, based on a total weight of the oral care product or the whitening composition thereof. In another example, the source of hydrogen peroxide may be present in an amount that provides hydrogen peroxide in an amount of from greater than 0.0 weight % to less than or equal to 10.0 weight %, about 0.5 weight % to about 9.5 weight %, about 1.0 weight % to about 9.0 weight %, about 1.5 weight % to about 8.5 weight %, about 2.0 weight %, to about 8.0 weight %, about 2.5 weight %, to about 7.5 weight %, about 3.0 weight % to about 7.0 weight %, about 3.5 weight %, to about 6.5 weight %, about 4.0 weight % to about 6.0 weight %, or about 4.5 weight % to about 5.5 weight %. In another implementation, the source of hydrogen peroxide may be present in an amount that provides from about 0.1 weight % to less than or equal to 2.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, or about 1.0 weight % to about 1.1 weight %, about 1.2 weight %, about 1.3 weight %, about 1.4 weight %, about 1.5 weight %, about 1.6 weight %, about 1.7 weight %, about 1.8 weight %, about 1.9 weight %, or about 2.0 weight %. In another example, the source of hydrogen peroxide may be present in an amount that provides hydrogen peroxide in an amount of from about 0.1 weight % to about 2.0 weight %, about 0.2 weight % to about 1.9 weight %, about 0.3 weight % to about 1.8 weight %, about 0.4 weight % to about 1.7 weight %, about 0.5 weight % to about 1.6 weight %, about 0.6 weight % to about 1.5 weight %, about 0.7 weight % to about 1.4 weight %, about 0.8 weight %, to about 1.3 weight %, about 0.9 weight % to about 1.2 weight %, or about 1.0 weight % to about 1.1 weight %. In yet another example, the source of hydrogen peroxide may be present in an amount that provides hydrogen peroxide in an amount less than or equal to 2.0 weight %, less than or equal to 1.8 weight %, less than or equal to 1.6 weight %, less than or equal to 1.4 weight %, less than or equal to 1.2 weight %, less than or equal to 1.0 weight %, less than or equal to 0.8 weight %, less than or equal to 0.6 weight %, or less than or equal to 0.4 weight %. In yet another implementation, the source of hydrogen peroxide may be present in an amount that provides from greater than 0.0 weight % to less than or equal to 35.0 weight % free hydrogen peroxide, based on a total weight of the oral care product or the whitening composition thereof. For example, the source of hydrogen peroxide may be present in an amount that provides hydrogen peroxide (e.g., free hydrogen peroxide) in an amount of from greater than 0.0 weight %, about 0.5 weight %, about 1.0 weight %, about 1.5 weight %, about 2.0 weight %, about 2.5 weight %, about 3.0 weight %, about 3.5 weight %, about 4.0 weight %, about 4.5 weight %, about 5.5 weight %, about 6.0 weight %, about 6.5 weight %, about 7.0 weight %, about 7.5 weight about 8.0 weight %, about 8.5 weight %, about 9.0 weight %, about 9.5 weight %, or about 10.0 weight % to about 12.0 weight %, about 14.0 weight %, about 16.0 weight %, about 18.0 weight %, about 20.0 weight %, about 22.0 weight %, about 24.0 weight %, about 26.0 weight %, about 28.0 weight %, about 30.0 weight %, about 32.0 weight %, about 34.0 weight %, or less than or equal to about 35.0 weight %, based on a total weight of the oral care product or the whitening composition thereof. In a typical implementation, the source of hydrogen peroxide may be present in an amount that provides hydrogen peroxide in an amount of about 35.0 weight % or less, or about 2.5 weight % or less, or about 2.0 weight % or less.

Cyclic Anhydride

The one or more cyclic anhydrides may be any compound or material capable of or configured to react with the hydrogen peroxide from the source of hydrogen peroxide to generate the whitening agent. Illustrative cyclic anhydrides may be or include, but are not limited to, maleic anhydride, succinic anhydride, naphthalenetetracarboxylic dianhydride, phthalic anhydride, chloromaleic anhydride, dichloromaleic anhydride, 3,4,5,6-tetrahydrophthalic anhydride, 3,4,5,6-tetrachlorophthalic anhydride, 3,4,5,6-tetrabromophthalic anhydride, and 1,4,5,6,7,7-hexachloro-(2,2,1)-5-heptene-2,3-dicarboxylic acid anhydride, and the like, and combinations thereof it should be appreciated that any two or more of the cyclic anhydrides may be combined or mixed with one another to control or adjust one or more properties of the anhydride mixture. For example, any two or more of the cyclic anhydrides may be mixed with one another to adjust the melting point and/or the solubility of the anhydride mixture in the oral care product or the whitening composition thereof.

In at least one implementation, the one or more cyclic anhydrides may be or include one or more polymer-based cyclic anhydrides, or polymeric materials containing a cyclic anhydride functionality along the polymer backbone or as a pendant functional group. Illustrative polymer-based cyclic anhydrides may be or include, but are not limited to, polyvinylmethylether/maleic anhydride (PVM/MA) copolymer, polymaleic anhydride, polystyrene/maleic anhydride (PS/MA) copolymer, polyethylene/maleic anhydride (PUMA) copolymer, polyepropylene/maleic anhydride (PP/MA) copolymer, polypropylene-graft-maleic anhydride, polyethylene-graft-maleic anhydride, and polyisoprene-graft-maleic anhydride.

The amount or concentration of the cyclic anhydride may vary widely. In at least one implementation, the amount of the cyclic anhydride may at least partially depend upon the amount of hydrogen peroxide provided by the source of hydrogen peroxides. For example, the cyclic anhydride may be provided in an effective amount or an amount sufficient to react with at least 50%, at least 60%, at least 70%, at least 80%, at least 90%, at least 95%, at least 98%, at least 99%, or at least 100% of the hydrogen peroxide provided by the source of hydrogen peroxide. As used herein, the expression "effective amount," may refer to an amount of a compound or a composition sufficient to induce a positive effect or benefit and/or an amount low enough to prevent or reduce a negative effect or serious side effects.

In a least one implementation, a weight ratio of the cyclic anhydride to the hydrogen peroxide provided by the source of hydrogen peroxide may be from about 0.1:1 to about 2:1. For example, the weight ratio of the cyclic anhydride to the hydrogen peroxide provided by the source of hydrogen peroxide may be from about 0.1:1, about 0.2:1, about 0.3:1, about 0.4:1, about 0.5:1, about 0.6:1, about 0.7:1, about 0.8:1, about 0.9:1, or about 1:1 to about 1.1:1, about 1.2:1, about 1.3:1, about 1.4:1, about 1.5:1, about 1.6:1, about 1.7:1, about 1.8:1, about 1.9:1, or about 2:1. In another example, the weight ratio of the cyclic anhydride to the hydrogen peroxide provided by the source of hydrogen peroxide may be from about 0.1:1 to about 2:1, about 0.2:1 to about 1.9:1, about 0.3:1 to about 1.8:1, about 0.4:1 to about 1.7:1, about 0.5:1 to about 1.6:1, about 0.6:1 to about 1.5:1, about 0.7:1 to about 1.4:1, about 0.8:1 to about 1.3:1, about 0.9:1 to about 12:1, or about 1:1 to about 1.1:1.

In a least one implementation, a molar ratio of the cyclic anhydride to the hydrogen peroxide provided by the source of hydrogen peroxide may be from about 0.1:1 to about 2:1. For example, the molar ratio of the cyclic anhydride to the hydrogen peroxide provided by the source of hydrogen peroxide may be from about 0.1:1, about 0.2:1, about 0.3:1, about 0.4:1, about 0.5:1, about 0.6:1, about 0.7:1, about 0.8:1, about 0.9:1, or about 1:1 to about 1.1:1, about 1.2:1, about 1.3:1, about 1.4:1, about 1.5:1, about 1.6:1, about 1.7:1, about 1.8:1, about 1.9:1, or about 2:1. In another example, the molar ratio of the cyclic anhydride to the hydrogen peroxide provided by the source of hydrogen peroxide may be from about 0.1:1 to about 2:1, about 0.2:1 to about 1.9:1, about 0.3:1 to about 1.8:1, about 0.4:1 to about 1.7:1, about 0.5:1 to about 1.6:1, about 0.6:1 to about 1.5:1, about 0.7:1 to about 1.4:1, about 0.8:1 to about 1.3:1, about 0.9:1 to about 1.2:1, or about 1:1 to about 1.1:1.

In a least one implementation, the cyclic anhydride may be provided in an amount of from about 0.1 weight % to about 5.0 weight %, based on a total weight of the oral care product or the whitening composition thereof. For example, the cyclic anhydride may be provided in an amount of from about 0.1 weight %, about 0.5 weight %, about 1.0 weight %, about 1.5 weight %, or about 2.0 weight % to about 3.0 weight %, about 3.5 weight %, about 4.0 weight %, about 4.5 weight %, or about 5.0 weight %. In another example, the cyclic anhydride may be provided in an amount of from about 0.1 weight % to about 5.0 weight %, about 0.5 weight % to about 4.5 weight %, about 1.0 weight % to about 4.0 weight %, about 1.5 weight % to about 3.5 weight %, or about 2.0 weight % to about 3.0 weight %. In another example, the cyclic anhydride may be provided in an amount greater than 0.0 weight % and less than or equal to 5.0 weight less than or equal to 4.5 weight %, less than or equal to 4.0 weight %, less than or equal to 3.5 weight %, less than or equal to 3.0 weight %, less than or equal to 2.5 weight %, less than or equal to 2.0 weight %, less than or equal to 1.5 weight %, less than or equal to 1.0 weight %, or less than or equal to 0.5 weight %.

In at least one implementation, the amount or concentration of the cyclic anhydride and/or the source of hydrogen peroxide may be at least partially determined by a target or desired concentration of the whitening agent to be generated in the oral care product or the whitening composition thereof. For example, in at least one implementation, the target or desired concentration of the whitening agent generated may be from about 100 ppm to about 20,000 ppm. For example, the target or desired concentration of the whitening agent generated may be from about 100 ppm, about 200 ppm, about 300 ppm, about 500 ppm, about 750 ppm, about 1,000 ppm, about 2,000 ppm, about 3,000 ppm, about 4,000 ppm, about 5,000 ppm, about 6,000 ppm, or about 7,000 ppm to about 9,000 ppm, about 10,000 ppm, about 11,000 ppm, about 12,000 ppm, about 13,000 ppm, about 14,000 ppm, about 15,000 ppm, about 16,000 ppm, about 17,000 ppm, about 18,000 ppm, about 19,000 ppm, or about 20,000 ppm. In another example, the target or desired concentration of the whitening agent generated may be from about 100 ppm to about 20,000 ppm, about 200 ppm to about 19,000 ppm, about 300 ppm to about 18,000 ppm, about 500 ppm to about 17,000 ppm, about 750 ppm to about 16,000 ppm, about 1,000 ppm to about 15,000 ppm, about 2,000 ppm to about 14,000 ppm, about 3,000 ppm to about 13,000 ppm, about 4,000 ppm to about 12,000 ppm, about 5,000 ppm to about 11,000 ppm, about 6,000 ppm to about 10,000 ppm, or about 7,000 ppm to about 9,000 ppm.

Whitening Agent

As discussed above, the cyclic anhydride and the hydrogen peroxide provided by the source of hydrogen peroxide may be reacted or otherwise contacted with one another to generate the whitening agent. In an exemplary implementation, the whitening agent may be a derivative of hydrogen peroxide, the molecule of which may contain one or more directly linked pairs of oxygen atoms. For example, the whitening agent may be a peroxy acid or peracid. In a typical implementation, mixing, combining, or otherwise contacting the cyclic anhydride and the hydrogen peroxide with one another may initiate the generation of the whitening agent. In a preferred implementation, the cyclic anhydride may be or include maleic anhydride and/or succinic anhydride, and the whitening agent may be or include maleic peracid and/or succinic peracid, respectively.

The amount or concentration of the whitening agent (e.g., peracid) generated from the oral care product or the whitening composition thereof may vary widely. In at least one implementation, the amount of the peracid generated may be from about 0.1 ppm to about 20,000 ppm based on a total weight of an oral care product (e.g, dentifrice, whitening gel, etc.) or the whitening composition thereof. For example, the amount of the peracid generated may be from about 0.1 ppm, about 0.5 ppm, about 1 ppm, about 5 ppm, about 10 ppm, about 15 ppm, about 20 ppm, about 50 ppm, about 100 ppm, about 150 ppm, about 200 ppm, about 300 ppm, about 500 ppm, about 600 ppm, about 700 ppm, about 800 ppm, or about 900 ppm to about 1,000 ppm, about 1,200 ppm, about 1,400 ppm, about 1,600 ppm, about 1,800 ppm, about 2,000 ppm, about 2,500 ppm, about 3,000 ppm, about 3,500 ppm, about 4,000 ppm, about 5,000 ppm, about 6,000 ppm, about 7,000 ppm, about 8,000 ppm, about 9,000 ppm, about 10,000 ppm, about 11,000 ppm, about 12,000 ppm, about 13,000 ppm, about 14,000 ppm, about 15,000 ppm, about 16,000 ppm, about 17,000 ppm, about 18,000 ppm, about 19,000 ppm, or about 20,000 ppm, based on a total weight of the oral care product or the whitening composition thereof. In another example, the amount of the peracid generated may be less than 0.1 ppm, less than 0.5 ppm, less than 1 ppm, less than 5 ppm, less than 10 ppm, less than 15 ppm, less than 20 ppm, less than 50 ppm, less than 100 ppm, less than 150 ppm, less than 200 ppm, less than 300 ppm, less than 500 ppm, less than 600 ppm, less than 700 ppm, less than 800 ppm, less than 900 ppm, less than 1,000 ppm, less than 1,200 ppm, less than 1,400 ppm, less than 1,600 ppm, less than 1,800 ppm, less than 2,000 ppm, less than 2,500 ppm, less than 3,000 ppm, less than 3,500 ppm, less than 4,000 ppm, less than 5,000 ppm, less than 6,000 ppm, less than 7,000 ppm, less than 8,000 ppm, less than 9,000 ppm, less than 10,000 ppm, less than 11,000 ppm, less than 12,000 ppm, less than 13,000 ppm, less than 14,000 ppm, less than 15,000 ppm, less than 16,000 ppm, less than 17,000 ppm, less than 18,000 ppm, less than 19,000, or less than 20,000, based on a total weight of the oral care product or the whitening composition thereof. In a typical implementation, the amount of the peracid generated is less than 20,000 ppm, based on a total weight of the oral care product or the whitening composition thereof.

In at least one implementation, the whitening agent may be generated within at least 3 minutes (min) from contacting the hydrogen peroxide and the cyclic anhydride with one another. In another implementation, the whitening agent may be generated within at least 3 minutes (min) from contacting the oral care product or the whitening composition thereof with water. For example, the whitening agent of the whitening composition may be generated in less than or equal to 3 min, less than or equal to 2.8 min, less than or equal to 2.6 min, less than or equal to 2.4 min, less than or equal to 2.2 min, less than or equal to 2.0 min, less than or equal to 1.8 min, less than or equal to 1.6 min, less than or equal to 1.4 min, less than or equal to 1.2 min, less than or equal to 1.0 min, less than or equal to 0.8 min, less than or equal to 0.6 min, or less than or equal to 0.4 min.

Vehicle

The whitening composition may form at least a portion of or be used in any one or more oral care products that are capable of contacting the whitening agent with the surfaces of the oral cavity or the teeth thereof. As used herein, the expression "whitening composition" may refer to a product or a composition thereof that in the ordinary course of usage is maintained in the oral cavity in an effective amount and in a time sufficient to contact at least a portion of the surfaces of the teeth for purposes of at least partially whitening the teeth. Illustrative oral care products may include, but are not limited to, a toothpaste (dentifrice), a prophylactic paste, a tooth powder, a tooth polish, a tooth gel (e.g., a whitening gel), a chewing gum, a lozenge, a mouthwash, a whitening strip, a paint-on gel, varnish, veneer, and tube, syringe or dental tray including a gel or paste, or a gel or paste coated on an application support such as dental floss or a toothbrush (e.g., a manual, electric, sound, a combination thereof or ultrasound toothbrush). In a preferred implementation, the whitening composition may form at least a portion of or be used in a mouthwash.

The whitening composition may include or be combined with an orally acceptable vehicle to form the oral care product (e.g., the mouthwash). As used herein, "orally acceptable vehicle" may refer to a suitable vehicle, ingredient, or combination of ingredients, which can be used to form and/or apply the oral care composition to the surfaces of the teeth in a safe and effective manner. It should be appreciated that the orally acceptable vehicle may include materials such as, but not limited to, one or more antibacterial agents, anticalculus agents, buffers, additional abrasives, sources of peroxide (e.g., hydrogen peroxide), alkali metal bicarbonate salts, thickening materials, humectants, water, surfactants, titanium dioxide, cooling agents, coloring agents, and the like, and combinations thereof. In an exemplary implementation, the orally acceptable vehicle may include a mixture of water, glycerin, and sorbitol. In another implementation, the orally acceptable vehicle may include water and glycerin. In yet another implementation, the whitening composition is combined with an orally acceptable vehicle including a hydrophilic phase and a hydrophobic phase, and optionally a hydrotrope to form a dual-phase mouthwash or a dual-phase mouthwash composition.

Polymers

The oral care product or the whitening composition thereof may include one or more polymers. Illustrative polymers that may be included in the oral care product or the whitening composition thereof may include polyvinylmethyl ether maleic acid copolymers and/or polysaccharides, such as cellulose derivatives, polysaccharide gums, and the like, and combinations thereof. The cellulose derivatives may include carboxymethyl cellulose, and the polysaccharide gums may include xanthum gum or carrageenan gum.

In at least one implementation, the whitening composition may include one or more copolymers, such as a polyvinylmethylether/maleic anhydride (PVM/MA) copolymer, polymaleic anhydride, polystyrene/maleic anhydride (PS/MA) copolymer, polyethylene/maleic anhydride (PE/MA) copolymer, polyepropylene/maleic anhydride (PP/MA) copolymer, polypropylene-graft-maleic anhydride, polyethylene-graft-maleic anhydride, and polyisoprene-graft-maleic anhydride, a phosphatelacrylate copolymer, and the like, and combinations thereof. As discussed above, the polymer-based cyclic anhydrides may be provided as a cyclic anhydride. For example, the polymer-based cyclic anhydrides may be reacted with the hydrogen peroxide to generate the whitening agent in an appreciable amount (e.g., greater than 200 ppm). In another implementation, the polymer-based cyclic anhydrides is not included as a cyclic anhydride. For example, the polymer-based cyclic anhydrides may not react with the hydrogen peroxide to generate the whitening agent in an appreciable amount (e.g., greater than 200 ppm). An illustrative PVM/MA copolymer may include those under the GANTREZ® brand, which is commercially available from ISP of Wayne, N.J.

Fluoride Ion Source

The oral care product or the whitening composition thereof may include one or more fluoride ion sources (e.g., soluble fluoride salts). A wide variety of fluoride ion-yielding materials may employed as sources of soluble fluoride. Examples of suitable fluoride ion-yielding materials may be found in U.S. Pat. No. 3,535,421 to Briner et al., U.S. Pat. No. 4,885,155 to Parran, Jr. et al., and U.S. Pat. No. 3,678,154 to Widder et al., the disclosures of which are incorporated herein by reference in their entirety to the extent they are consistent with the present disclosure. Illustrative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In a preferred implementation, the fluoride ion source includes sodium fluoride. The amount of the fluoride ion source present in the whitening composition may be less than 0.08 wt %. For example, the amount of the fluoride ion source present in the whitening composition may be less than 0.08 weight %, less than 0.07 weight %, less than 0.06 weight %, less than 0.05 weight %, or less than 0.04 weight %. In another implementation, the fluoride ion source is present in an amount to provide fluoride ions in a total amount of about 100 to about 20,000 ppm, about 200 to about 5,000 ppm, or about 500 to about 2,500 ppm.

Surfactants

The oral care product or the whitening composition thereof may include one or more surfactants. For example, the whitening composition may include one or more anionic surfactants, one or more cationic surfactants, one or more zwitterionic surfactants, one or more nonionic surfactants, and mixtures thereof. Examples of suitable surfactants may be found in U.S. Pat. No. 3,959,458 to Agricola et al., U.S. Pat. No. 3,937,807 to Haefele, and U.S. Pat. No. 4,051,234 to Gieske et al., the disclosures of which are incorporated herein by reference in their entirety to the extent they are consistent with the present disclosure.

In at least one implementation, the oral care product or the whitening composition thereof includes at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate. Illustrative anionic surfactants may also include higher alkyl sulfates. As used herein, "higher alkyl" refers to $C_{6-30}$ alkyl. For example, in a preferred implementation the anionic surfactant is sodium lauryl sulfate. The anionic surfactants may also include higher alkyl-ether sulfates. For example, the anionic surfactants may have a formula $CH_3(CH_2)_mCH_2(OCH_2CH_2)_nOSO_3X$, where m is 6-16, n is 1-6, and X is Na or K. In an exemplary implementation, m is 10, and n is 2, 3, or 4, and X is Na or K. For example, the anionic surfactant may be sodium laureth-2 sulfate $(CH_3(CH_2)_{10}CH_2(OCH_2CH_2)_2OSO_3Na)$. In another implementation, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. In an exemplary implementation, the anionic surfactant is a water soluble salt of alkyl sulfates having from 10 to 18 carbon atoms in the alkyl radical and water soluble salts of sulfonated monoglycerides of fatty acids having from 10 to 18 carbon atoms. For example, the anionic surfactant may be or include, sodium lauryl sulfate, sodium lauroyl sarcosinate, sodium coconut monoglyceride sulfonates, or the like, and mixtures thereof.

In at least one implementation, the oral care product or the whitening composition thereof may include at least one nonionic surfactant. Accordingly, the oral care product or the whitening composition thereof may include at least one anionic surfactant, at least one nonionic surfactant, or both an anionic surfactant and a nonionic surfactant. The nonionic surfactant may function as an emulsifier. Illustrative nonionic surfactants may include, but are not limited to, poloxamers or the like. For example, the nonionic surfactants may include polysorbate 20, poloxamer 407, poloxamer 338, or the like, and mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, and combinations thereof. In a preferred implementation, the nonionic surfactant is polysorbate 20.

The amount of any one or more of the surfactants in the oral care product or the whitening composition thereof may be from about 0.010 wt %, about 0.020 wt %, about 0.030 wt %, about 0.040 wt %, about 0.045 wt %, about 0.049 wt %, or about 0.050 wt % to about 0.051 wt %, about 0.055 wt %, about 0.060 wt %, about 0.065 wt %, about 0.070 wt %, about 0.075 wt %, about 0.080 wt %, or greater. In another example, the amount of any one or more of the surfactants in the oral care product or the whitening composition thereof may be about 0.010 wt % to about 0.090 wt %, about 0.020 wt % to about 0.080 wt %, about 0.030 wt % to about 0.070 wt %, about 0.040 wt % to about 0.060 wt %, about 0.045 wt % to about 0.055 wt %, or about 0.050 wt % to about 0.051 wt %. In yet another example, the amount of any one or more of the surfactants in the oral care product or the whitening composition thereof may be greater than 0.010 wt %, greater than 0.020 wt %, greater than 0.030 wt %, greater than 0.040 wt %, greater than 0.045 wt %, greater than 0.049 wt %, or greater than 0.050 wt %. The amount of any one or more of the surfactants in the oral care product or the whitening composition thereof may also be from about 0.10 wt %, about 0.20 wt %, about 0.30 wt %, about 0.40 wt %, about 0.45 wt %, about 0.49 wt %, or about 0.50 wt % to about 0.51 wt %, about 0.55 wt %, about 0.60 wt %, about 0.65 wt %, about 0.70 wt %, about 0.75 wt %, about 0.80 wt %, or greater. In another example, the amount of any one or more of the surfactants in the oral care product or the whitening composition thereof may be about 0.10 wt % to about 0.90 wt %, about 0.20 wt % to about 0.80 wt %, about 0.30 wt % to about 0.70 wt %, about 0.40 wt % to about 0.60 wt %, about 0.45 wt % to about 0.55 wt %, or about 0.50 wt % to about 0.51 wt %. In yet another example, the amount of any one or more of the surfactants in the oral care product or the whitening composition thereof may be greater than 0.10 wt %, greater than 0.20 wt %, greater than 0.30 wt %, greater than 0.40 wt %, greater than 0.45 wt %, greater than 0.49 wt %, or greater than 0.50 wt %.

Flavoring Agents

The oral care product or the whitening composition thereof may also include one or more flavoring agents. Illustrative flavoring agents may include, but are not limited to, essential oils and various flavoring aldehydes, esters, alcohols, and the like. The flavoring agents may also include, but are not limited to, sweeteners, sucralose, dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof (e.g., sodium saccharin), dipeptide-based intense sweeteners, cyclamates, dihydrochalcones and mixtures thereof. Examples of the essential oils include oils of spearmint, peppermint, wintergreen, sassafras, clove, sage, eucalyptus, marjoram, cinnamon, lemon, lime, grapefruit, and orange. In another example, the flavoring agents may include menthol, carvone, and anethole. In a preferred implementation, the flavoring agent includes peppermint and spearmint. In a more preferred implementation, the flavoring agent includes a Firmenich Newman Flavor. The amount of the flavoring agent in the oral care product or the whitening composition thereof may be less than 1.0 wt %, less than 0.9 wt %, less than 0.8 wt %, or less than 0.7 wt %. For example, the amount of the flavoring agent in the oral care product or the whitening composition thereof may be about 0.0 wt % to about 1.0 wt %, about 0.5 wt % to about 0.9 wt %, about 0.7 wt % to about 0.8 wt %. In a preferred implementation, the amount of the flavoring agent in the oral care product or the whitening composition thereof is about 0.75 wt % to about 0.80 wt %.

Humectants

The oral care product or the whitening composition thereof may include one or more humectants. The humectants may be capable of or configured to reduce evaporation and lower water activity. It should be appreciated that the humectants may also be capable of imparting desirable sweetness or flavor to the oral care product or the whitening composition thereof. Illustrative humectants may include, but are not limited to polyhydric alcohols, such as glycerin, sorbitol, xylitol, propylene glycol, as well as other polyols, and mixtures thereof.

Water

The oral care product or the whitening composition thereof may include water. Water of the oral care product or the whitening composition thereof may be deionized and free of organic impurities. Water may make up the balance of the oral care product or the whitening composition thereof. For example, the amount of water in the oral care product or the whitening composition thereof may be from about 10 wt % to 90 wt %, about 40 wt % to about 85 wt %, or about 60 wt % to about 80 wt %. In another example, the amount of water in the oral care product or the whitening composition thereof may be at least 60 wt %, at least 65 wt %, at least 70 wt %, at least 78 wt %, or at least 79 wt %. The amount of water in the oral care product or the whitening composition thereof may include free water added and water introduced with other components or materials of the oral care product or the whitening composition thereof. For example, the amount of the water in the oral care product or the whitening composition thereof may include free water and water associated with the humectants, flavoring agents, or any other component of the oral care product or the whitening composition thereof.

Additional Components/Ingredients

The oral care product or the whitening composition thereof may optionally include one or more additional components or ingredients. For example, the oral care product or the whitening composition thereof may include one or more antimicrobial agents such as, methylisothiazolinone (MIT), sodium benzoate, potassium sorbate, and combinations thereof. In another example, the oral care product or the whitening composition thereof may include one or more antibacterial agents selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC), phenolic antiseptics, hexetidine, octenidine, sanguinarine, povidone iodine, delmopinol, salifluor, other metal ions (e.g., stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol, and other piperidine derivatives, nicin preparations, chlorite salts; and mixtures of any of the foregoing. In an exemplary implementation, the antibacterial agent includes cetylpyridinium chloride (CPC).

The oral care product or the whitening composition thereof may optionally include one or more pH modifying agents. For example, the oral care product or the whitening composition thereof may include one or more acidifying agents and/or one or more basifying agents to reduce and/or increase the pH, respectively. The oral care product or the whitening composition thereof may also include one or more buffering agents to control or modulate the pH within a predetermined or desired range. Illustrative buffering agents may include, but are not limited to, sodium bicarbonate, sodium phosphate, sodium hydroxide, sodium carbonate, sodium acid pyrophosphate, citric acid, sodium citrate, and mixtures thereof. Sodium phosphate may include, monosodium phosphate ($NaH_2PO_4$), disodium phosphate ($Na_2HPO_4$), trisodium phosphate ($Na_3PO_4$), and mixtures thereof. In a preferred implementation, the buffering agent is anhydrous sodium phosphate dibasic or disodium phosphate.

In at least one implementation, the acidifying, buffering, and/or buffering agents may be included in the oral care product or the whitening composition thereof to provide the oral care composition with a pH between 2 to 10, 2 to 8, 3 to 9, 4 to 8, 6 to 10, or 7 to 9. Additional orally acceptable pH modifying agent may be used, including without limitation carboxylic, phosphoric, and sulfonic acids, acid salts (e.g., monosodium citrate, disodium citrate, monosodium malate, etc.), alkali metal hydroxides, such as sodium hydroxide, carbonates, such as sodium carbonate, bicarbonates, sesquicarbonates, borates, silicates, phosphates (e.g., monosodium phosphate, trisodium phosphate, pyrophosphate salts, etc. imidazole and mixtures thereof. The one or more pH modifying agents may be optionally present in an amount effective to maintain the oral care product or the whitening composition thereof in an orally acceptable pH range. In a preferred implementation, the buffering agent includes anhydrous sodium phosphate dibasic or disodium phosphate, and phosphoric acid (e.g., syrupy phosphoric acid; 85%-food Grade).

Methods

In various implementations, the present disclosure provides methods to whiten surfaces of teeth in a human or animal subject in need thereof. As used herein, "animal subject" includes non-human mammals such as canines, felines, and horses. The methods may include contacting the surfaces of the teeth with the whitening composition or the whitening agent of the present disclosure. Contacting the whitening composition with the surfaces of the teeth may include brushing, flossing, irrigating, wiping, rinsing (lavage of oral cavity), foam/gel and in-tray application, masticating, spraying, painting, and the like.

In various implementations, the oral care product, or the whitening composition thereof, prepared in accordance with the present disclosure may be applied regularly to an oral surface, for example on a daily basis, at least one time daily for multiple days, or alternately every second or third day. In some implementations, the oral care product or the whitening composition thereof is applied to the oral surfaces from 1 to 3 times daily, for at least 2 weeks up to 8 weeks, from four months to three years, or more, up to a lifetime.

In some implementations, the oral care product (e.g., the mouthwash) or the whitening composition thereof may be applied directly to the teeth using a delivery device, such as a pen, (e.g., a COLGATE® whitening pen or a COLGATE® ACTIS™ whitening pen, Colgate-Palmolive Company, New York, N.Y.), a liquid stick having an applicator, such as a felt tip, brush, roller ball, or non-woven pad, sufficient to effect whitening.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The generation of peracid from an oral care composition, namely a mouthwash, was evaluated via HPLC and UV/Vis. Since peracid is not visible via UV-Vis, secondary compounds that are visible or absorb in the UV-Vis spectrum were derived from the generated peracid via successive oxidation reactions.

To simulate the generation of peracid, namely maleic peracid, about 100 mg (0.5 weight % to mouthwash) of a cyclic anhydride, namely maleic anhydride, and 100 mg (0.5 weight % to mouthwash) of sodium carbonate, a pH modifying agent, was combined with 20.0 g of a mouthwash containing 2 weight % hydrogen peroxide. The mouthwash mixture was agitated for 1 minute, and 1.0 mL of the agitated mixture was diluted with water to 20 mL. To derive the secondary compounds, 360 µL of the diluted mixture was then transferred to a microfuge tube containing 40 µL of 1.3 M phosphoric acid and mixed or agitated to reach a final pH of less than 3, thereby terminating the maleic anhydride ring opening reaction in generating peracid. 100 µL of mixed solution was then transferred to an container/vial containing 300 µL, of water and 100 µL of a methyl tolyl sulfide (MTS) reagent, and mixed or agitated in the dark for at least 10 min, thereby reacting the peracid with the MTS reagent to produce methyl tolyl sulfoxide (MTSO) and acetic acid (AcOH). Then 400 µL of acetonitrile and 100 µL of a triphenyl phosphine (TPP) reagent was added to the solution and allowed to react in the dark for 30 min. After 30 min, 100 µL of acetonitrile was added and mixed thoroughly, and the resulting solution was analyzed via HPLC.

The calculated concentration of MTSO was then corrected for dilution (i.e., during the acid quench step) and total reaction volume. It should be appreciated that the molar concentration of the peracid is equivalent to the calculated concentration of MTSO including the aforementioned corrections. The amount of the peracid generated from the hydrogen peroxide mouthwash and the maleic anhydride is summarized in Table 1.

TABLE 1

Amount of Maleic Peracid Generated in Mouthwash

| Weight of MA (g) | 0 | 0.1 | 0.2 | 0.4 | 0.8 |
|---|---|---|---|---|---|
| Weight of SC (g) | 0 | 0.1 | 0.2 | 0.4 | 0.8 | soakings for each treatment). The L*, a*, b* values after each treatment were compared to the baseline values to calculate the change in the whiteness of each of the teeth. It should be appreciated that the whiteness index (W*) is a measure of overall color change relative to pure white, and is given by formula (1), and the change in whiteness index ($\Delta W^*$) is measured by formula (2). The change in whiteness index ($\Delta W^*$) is summarized in Table 2.

$$W^* = ((L^*-100)^2 + (a^*)^2 + (b^*)^2)^{1/2} \quad (1)$$

$$\Delta W^* = W^*_{treated} - W^*_{baseline} \quad (2)$$

TABLE 2

Whitening Efficacy ($\Delta W^*$) for In Vitro Treatments with Whitening Compositions

| | | Number of Treatments | | | | | | |
|---|---|---|---|---|---|---|---|---|
| | | 0 | 2 | 4 | 6 | 8 | 10 | 12 | 14 |
| MW + 0% MA + 0% SC; pH = 4.5 | $\Delta W^*$ | 0 | 0.607 | 1.232 | 1.250 | 1.387 | 1.506 | 2.09 | 1.731 |
| MW + 0.5% SC; pH = 6.0 | $\Delta W^*$ | 0 | 0.732 | 1.387 | 1.736 | 1.412 | 1.661 | 1.784 | 2.292 |
| MW + 1% MA + 1% SC; pH = 5.3 | $\Delta W^*$ | 0 | 1.556 | 2.471 | 2.898 | 3.852 | 3.584 | 4.538 | 5.058 |
| MW + 2% MA + 2% SC; pH = 6.1 | $\Delta W^*$ | 0 | 2.536 | 3.954 | 5.359 | 6.437 | 7.163 | 8.064 | 8.711 |

TABLE 1-continued

Amount of Maleic Peracid Generated in Mouthwash

| Weight of Mouthwash (g) | 0 | 20.0 | 20.0 | 20.0 | 20.0 |
|---|---|---|---|---|---|
| Maleic Peracid (ppm) Measured | 0 | 5,629 | 8,938 | 15,737 | 19,930 |

As illustrated in Table 1, when more maleic anhydride (MA) and sodium carbonate (SC) were mixed with 20.0 g of a mouthwash containing 2.0 weight % hydrogen peroxide, more maleic peracid was generated. For example, about 5,600 ppm maleic peracid was formed in the when 0.1 g of MA and 0.1 g of SC were added to 20.0 g of mouthwash and over 15,000 ppm of maleic peracid was formed when 0.4 g maleic anhydride and 0.4 g of SC were added to the mouthwash. It should be appreciated that higher concentration of the peracid generated in mouthwash solution would lead to better whitening efficacy.

Example 2

The whitening efficacy of whitening compositions including 2 weight % hydrogen peroxide mouthwash with varying amounts of maleic anhydride and sodium carbonate was evaluated in vitro. Particularly, artificially stained bovine incisors individually mounted to resin blocks were obtained from Therametric Technologies, Inc. The artificially stained bovine teeth selected for the analysis had L* values from about 58 to about 63.

Solutions of 20 g of the 2 weight % hydrogen peroxide mouthwash (MW) with varying amounts of maleic anhydride (MA) and sodium carbonate (SC) were prepared. The bovine teeth were soaked in each of the respective solutions for 1 minute after combining the mouthwash with the maleic anhydride and sodium carbonate. Each of the bovine teeth was soaked in the solution twice to provide one treatment.

The L*, a*, and b* values were measured with a handheld spectrophotometer after each treatment (one minute It was surprisingly and unexpectedly discovered, as demonstrated in Table 2, that the combination of maleic anhydride (MA) and sodium carbonate (SC) with a mouthwash (MW) containing 2.0 weight % hydrogen peroxide significantly enhanced the whitening efficacy of the whitening compositions. Particularly, the whitening composition including the maleic anhydride and the sodium carbonate provided whiter teeth at a faster rate. For example, the mouthwash including 1% MA and 1% SC had a whitening efficacy ($\Delta W$) of about 5.1, which was about three times the whitening efficacy of the MW including the hydrogen peroxide alone with 14 treatments. The enhanced whitening efficacy ($\Delta W$) was not attributed to the change in pH, as the whitening composition including the MW and 0.5% SC exhibited similar whitening efficacy ($\Delta W$) as compared to the MW alone.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A mouthwash composition, comprising an orally acceptable vehicle, sodium carbonate, a source of hydrogen peroxide that provides hydrogen peroxide, and a cyclic anhydride that generates a peracid with the hydrogen peroxide provided by the source of hydrogen peroxide; and
   wherein the molar ratio of the cyclic anhydride to the hydrogen peroxide provided by the source of hydrogen peroxide is from about 0.8:1 to about 1.3:1;
   wherein the orally acceptable vehicle further comprises one or more ingredient selected from antibacterial agents, anticalculus agents, humectants, surfactants and cooling agents; and wherein the cyclic anhydride is not a polymer-based cyclic anhydride.

2. The mouthwash composition of claim 1, wherein the source of hydrogen peroxide comprises at least one of hydrogen peroxide, urea peroxide, calcium peroxide, sodium perborate, a polyvinylpyrrolidone (PVP) hydrogen peroxide complex, and sodium percarbonate.

3. The mouthwash composition of claim 1, wherein the source of hydrogen peroxide is present in the whitening composition in an amount effective to provide less than or equal to 2.0 weight % of the hydrogen peroxide.

4. The mouthwash composition of claim 1, wherein the cyclic anhydride is at least one of maleic anhydride, succinic anhydride, naphthalenetetracarboxylic dianhydride, phthalic anhydride, chloromaleic anhydride, and dichloromaleic anhydride.

5. The mouthwash composition of claim 1, wherein the cyclic anhydride is maleic anhydride.

6. The mouthwash composition of claim 1, wherein the peracid is maleic peracid.

7. The mouthwash composition of claim 1, wherein the cyclic anhydride is succinic anhydride.

8. The mouthwash composition of claim 7, wherein the peracid is succinic peracid.

9. The mouthwash composition of claim 1, wherein the molar ratio of the cyclic anhydride to the hydrogen peroxide provided by the source of hydrogen peroxide is about 1:1.

10. The mouthwash composition of claim 1, wherein the peracid is generated in less than or equal to three minutes after contacting the hydrogen peroxide and the cyclic anhydride with one another.

11. The mouthwash composition of claim 1, further comprising a fluoride ion source.

12. The mouthwash composition of claim 1, further comprising a surfactant.

13. A method for whitening teeth of a subject, comprising contacting the mouthwash composition of claim 1 with surfaces of the teeth of the subject in need thereof.

14. A method for generating a whitening agent in a mouthwash composition, comprising contacting a cyclic anhydride and hydrogen peroxide with one another in the presence of sodium carbonate, wherein the whitening agent is a peracid; and wherein the cyclic anhydride is not a polymer-based cyclic anhydride.

* * * * *